United States Patent [19]
Komer

[11] Patent Number: 5,962,536
[45] Date of Patent: Oct. 5, 1999

[54] INJECTABLE PROPOFOL FORMULATIONS

[76] Inventor: Gene Komer, 2817 W. County Rd. 54G, Fort Collins, Colo. 80524

[21] Appl. No.: 09/127,082

[22] Filed: Jul. 31, 1998

[51] Int. Cl.⁶ .................................................. A61K 31/05
[52] U.S. Cl. ............................................................ 514/731
[58] Field of Search ............................................. 514/731

[56] References Cited

U.S. PATENT DOCUMENTS

| | | | |
|---|---|---|---|
| 4,772,460 | 9/1988 | Malook | 424/10 |
| 5,446,070 | 8/1995 | Mantelle | 514/772.6 |
| 5,496,537 | 3/1996 | Henry | 424/45 |
| 5,707,996 | 1/1998 | Parrinello | 514/256 |

OTHER PUBLICATIONS

Tonner, P.H. et al. "The General Anesthetic Potency of Propofol and Its Dependence on Hydrostatic Pressure"; (1992) *Anesthesiology* 77:926–931.

Advertising brochure for Nuflor® (Florfenicol) Injectable Solution; "Heads Up Therapy for BRD" published (1996) by Schering Corporation U.S.A.

Driscoll, D.F. et al., "Particle Size Distribution of Propofol Injection Ampules and Vials: The Benefits of Filtration"; (1997) *Int. J. or Pharm. Compounding* 1(2).

*Primary Examiner*—Raymond Henley, III
*Attorney, Agent, or Firm*—Greenlee Winner and Sullivan PC

[57] ABSTRACT

The invention provides injectable formulations of propofol using N-methylpyrrolidone or 2-pyrrolidone as a solvent. Formulations of the invention are useful in all medical and veterinary indications when propofol is presently used. In addition, combinations of propofol and an appropriate toxin are useful for fast-acting, humane, veterinary euthanasia injectable compositions. N-methylpyrrolidone-propylene glycol formulations are inherently bacteriostatic, thereby eliminating one of the problems associated with currently available formulations.

19 Claims, No Drawings

INJECTABLE PROPOFOL FORMULATIONS

Propofol is a quick-acting anesthetic of short duration marketed for human anesthesia under the trade name Diprivan by Stuart Pharmaceuticals and marketed for anesthesia in dogs by Schering-Plough Animal Health Corporation under the trade name Rapinovet and by Abbott Laboratories under the trade name PropoFlo.

Propofol is poorly soluble in water. The early human product was solubilized in a surfactant known as Cremophor EL. There were many instances of allergic reactions to the surfactant, requiring that the product be reformulated. At present all three propofol products are marketed as a cloudy emulsion of soybean oil, lecithin and other minor ingredients.

The currently available product contains no antimicrobial preservatives, making it particularly susceptible to microbial contamination after opening because of the nutrient base. Major problems associated with infections in patients anesthetized with propofol have been reported. Stuart Pharmaceuticals sent a "Dear Doctor" letter to anesthesiologists in 1990 addressing the post-operative incidence of fevers and infections in patients anesthetized with Diprivan. An additional problem has been encountered with the use of sterile glass ampoules for packaging propofol suspensions. Occasionally, glass particles contaminate the suspension after the ampoule is cracked open, leading to the inconvenient necessity of filtering the suspension prior to injection.

Propofol is 2,6-diisopropylphenol. It is an extremely fast-acting anaesthetic of short duration, administered intravenously. Its medical and veterinary use is primarily for rapid anesthesia, often in conjunction with slower-onset anesthetics, and for procedures of short duration. Maximum solubility in water is reported as 1.0±0.02 $\mu$M at 22.5° C.; Tonner, P. H. et al. (1992) Anesthesiology 77:926–931. Currently, only the soybean oil suspension of propofol is available in the market, despite the disadvantages thereof, which have been known for many years.

N-methylpyrrolidone and 2-pyrrolidone have not been widely used in the formulation of injectable medicaments. U.S. Pat. No. 4,772,460 discloses the use of N-methylpyrrolidone for parenteral administration of oxytetracycline. U.S. Pat. No. 5,707,996 describes solubilization of trimethoprim and sulfadiazine. The antibiotic florfenicol is marketed as an injectable formulation in N-methylpyrrolidone, propylene glycol and polyethylene glycol for intramuscular injection in cattle.

SUMMARY OF THE INVENTION

The invention provides injectable formulations of propofol using N-methylpyrrolidone or 2-pyrrolidone as a solvent. Formulations of the invention can include other components including other pharmacologic agents, diluents, co-solvents, expanders, dispersants, surface-active agents and the like, as will be understood by those skilled in the formulation art and as appropriate for the active ingredients of the formulation. Formulations of the invention are useful in all medical and veterinary indications when propofol is presently used. In addition, combinations of propofol and an appropriate toxin are useful for fast-acting, humane, veterinary euthanasia injectable compositions. N-methylpyrrolidone-propylene glycol formulations are inherently bacteriostatic, thereby eliminating one of the problems associated with currently available formulations.

DETAILED DESCRIPTION OF THE INVENTION

The solubilization of propofol in N-methylpyrrolidone and other physiologically acceptable co-solvents such as propylene glycol and water provides significant advantages in the manufacture, use, pharmaceutical elegance and stability of propofol injectable products. Not only is the N-methylpyrrolidone-propofol product water clear, it does not provide a nutrient base for microbial growth. In fact, N-methylpyrrolidone-propylene glycol mixtures are bacteriostatic.

Propofol formulations have been found to be completely stable for at least 32 months storage at room temperature.

The present invention is not only superior for propofol anesthesia injectables, but also for making a veterinary euthanasia injectable composition. The 1993 AVMA Panel on Euthanasia recommended use of barbiturates such as pentobarbital for small animal euthanasia. The barbiturates are narcotic controlled drugs regulated by the DEA. There is considerable paperwork involved as well as having many record-keeping and security requirements such as a locked safe. Propofol provides rapid onset of anesthesia so that an animal to be euthanized experiences minimal discomfort as the lethal effects of the euthanizing toxin take hold. The combination is more humane than previously approved formulations, such as T-61, which have been shown, in some instances, to afford a period of consciousness even as respiratory depression is occurring. A preferred composition for euthanizing purposes includes propofol and a curariform agent.

Formulations of propofol in N-methylpyrrolidone, 2-pyrrolidone, or mixtures thereof, can contain from 1% to 20% (w/v) propofol. Therapeutic dosage is well-known in the art, usually delivered at 10–20 mg propofol/ml. The ability to provide a more concentrated formulation has several advantages. The anesthetic can be delivered in a smaller volume. Any side effects due to other formulation components can be minimized. If desired, a larger amount of the anesthetic can be delivered in a single dose.

A formulation of the invention can simply be propofol dissolved in N-methyl-pyrrolidone, 2-pyrrolidone, or mixtures thereof. Other formulations can include propylene glycol or other non-toxic polyhydroxy alcohols, including, e.g., polyethylene glycol. Such formulations can contain up to 90% (v/v) propylene glycol or other non-toxic polyhydroxy alcohol as a diluent. N-methylpyrrolidone, 2-pyrrolidone or a mixture thereof can constitute as little as 5% (w/v). The formulations of the invention can include water, quantum sufficit (q.s.) up to 50% (v/v).

Preferred euthanizing formulations include propofol in combination with a skeletal muscle relaxant, capable of inhibiting muscle contraction. Suitable muscle relaxants include succinylcholine chloride, gallamine and curariform agents, such as mivacurium, atracurium, cisatracurium, vecuronium, rocuronium, pancuronium, metocurine, tubocurarine, doxicurium, pipecuronium, and suitable salts thereof, as well as other inhibitors of muscle contraction acting at the neuromuscular junction.

Optional ingredients include a local anesthetic agent of the type well-known in the art, e.g., lidocaine, and a preservative of a type well-known in the art, such as benzyl alcohol. Examples of suitable formulations are as follows.

| Example 1: Anesthesia Formulation #1 | |
|---|---|
| Propofol | 10 mg/ml |
| N-Methylpyrrolidone | 30% w/v |
| Propylene Glycol | 40% w/v |
| Water for Injection, qs | ~31% v/v |

-continued

Example 2: Anesthesia Formulation #2

| | |
|---|---|
| Propofol | 20 mg/ml |
| N-Methylpyrrolidone | 30% w/v |
| Propylene Glycol | 40% w/v |
| Water for injection, qs | ~30% v/v |

Example 3: Euthanasia Formulation #1

| | |
|---|---|
| Propofol | 10 mg/ml |
| Succinylcholine chloride | 20 mg/ml |
| Lidocaine HCl | 20 mg/ml |
| N-Methylpyrrolidone | 30% w/v |
| Propylene Glycol | 40% w/v |
| Benzyl Alcohol | 1.5% v/v |
| Purified Water | qs |

Example 4: Euthanasia Formulation #2

| | |
|---|---|
| Propofol | 10 mg/ml |
| Pancuronium Bromide | 2 mg/ml |
| Lidocaine | 20 mg/ml |
| N-Methylpyrrolidone | 40% w/v |
| Propylene Glycol | 30% w/v |
| Benzyl Alcohol | 2% v/v |
| Purified Water | qs |

I claim:

1. An injectable anesthetic formulation comprising propofol and N-methyl pyrrolidone, or 2-pyrrolidone, or a mixture thereof.

2. The formulation of claim 1 wherein the propofol concentration is 1%–20% w/v.

3. The formulation of claim 1 further comprising a non-toxic polyhydroxy alcohol.

4. The formulation of claim 3 wherein the polyhydroxy alcohol is propylene glycol.

5. The formulation of claim 4 comprising up to 90% (v/v) propylene glycol.

6. The formulation of claim 3 wherein the polyhydroxy alcohol is polyethylene glycol.

7. The formulation of claim 3 further comprising water.

8. A formulation according to claim 7 having the composition: propofol, 10 mg/ml; N-methylpyrrolidone 30% (w/v), propylene glycol 40% w/v and water quantum sufficit.

9. A formulation according to claim 7 having the composition: Propofol, 20 mg/ml; N-methylpyrrolidone 30% (w/v); propylene glycol, 40% (w/v) and water quantum sufficit.

10. A formulation for veterinary euthanasia comprising propofol, a skeletal muscle relaxant and N-methyl pyrrolidone, 2-pyrrolidone or a mixture thereof.

11. The formulation of claim 10 wherein the propofol concentration is 1%–20% w/v.

12. The formulation of claim 10 further comprising a non-toxic polyhydroxy alcohol.

13. The formulation of claim 12 wherein the polyhydroxy alcohol is propylene glycol.

14. The formulation of claim 13 comprising up to 90% (v/v) propylene glycol.

15. The formulation of claim 12 wherein the polyhydroxy alcohol is polyethylene glycol.

16. The formulation of claim 12 further comprising water.

17. A formulation according to claim 10 wherein the skeletal muscle relaxant is selected from the group consisting of succinyl, choline chloride, gallamine, miracurium, atracurium, cisatracurium, vecuronium, rocuronium, pancuronium, metocurine, tubocurarine, doxicurium, pipecuronium, and suitable salts thereof.

18. A formulation according to claim 16 having the composition: propofol 10 mg/ml; succinylcholine chloride, 20 mg/ml; lidocaine HCl, 20 mg/ml, N-methylpyrrolidone, 30% (w/v); propylene glycol, 40% (w/v); benzyl alcohol, 1.5% v/v; and water, quantum sufficit.

19. A formulation according to claim 16 having the composition: propofol, 10 mg/ml; pancuronium bromide, 2 mg/ml; lidocaine, 20 mg/ml; N-methylpyrrolidone, 40% (w/v); propylene glycol, 30% (w/v); benzyl alcohol, 2% v/v; and water, quantum sufficit.

* * * * *